United States Patent [19]

Date et al.

[11] Patent Number: 5,384,368
[45] Date of Patent: Jan. 24, 1995

[54] PROCESS FOR PRODUCING WATER ABSORBENT RESIN

[75] Inventors: Masashi Date, Osaka; Takashi Sumiya; Hitoshi Takai, both of Kyoto, all of Japan

[73] Assignee: Sanyo Chemical Industries, Ltd., Japan

[21] Appl. No.: 201,234

[22] Filed: Feb. 24, 1994

[30] Foreign Application Priority Data

Mar. 31, 1993 [JP] Japan .................................. 5-98832

[51] Int. Cl.$^6$ ................................................ C08F 8/30
[52] U.S. Cl. ..................................... 525/186; 525/185; 525/187; 525/329.9; 525/375
[58] Field of Search ................. 525/185, 186, 187, 375

[56] References Cited

U.S. PATENT DOCUMENTS

| | | | |
|---|---|---|---|
| 4,189,468 | 2/1989 | Vanlerberghe et al. | 525/423 |
| 4,536,552 | 8/1985 | Killat et al. | 525/451 |
| 5,296,541 | 3/1994 | Swarup et al. | 525/375 |

FOREIGN PATENT DOCUMENTS 57-44627  3/1982  Japan .

*Primary Examiner*—Bernard Lipman
*Attorney, Agent, or Firm*—Wegner, Cantor, Mueller and Player

[57] ABSTRACT

The present invention relates to a process for producing water absorbent resin comprising a step of adding a high-molecular crosslinking agent which has at least 2 azetidinium salt groups in the molecule and has at least 1000 weight-average molecular weight to the water absorbent resin paticles having carboxylic groups and carboxylic acid salt groups and a step of efficiently crosslinking the vicinity of the surface of the water absorbent resin particles. In the process for producing water absorbent resin according to the present invention, the use of high-molecular crosslinking agent achieves less permeation of the crosslinking agent into the water absorbent resin particles and enables efficient crosslinking of the vicinity of the surface of the water absorbent resin particles. Consequently, the water absorbent resin having high water absorbency both under pressure-free state and under loading can be manufactured. Because the crosslinking agent contains a large amount of azetidinium salt groups highly reactive to carboxylic acid groups or carboxylic acid salt groups in the molecule, the water absorbent resin having high crosslinking efficiency, good safety, and good flowability can be manufactured.

9 Claims, No Drawings

PROCESS FOR PRODUCING WATER ABSORBENT RESIN

BACKGROUND OF THE INVENTION

1. FIELD OF THE INVENTION

The present invention relates to a process for producing water absorbent resin. More specifically, it relates to a process for producing water absorbent resin having high water absorbency under loading and high safety.

2. DESCRIPTION OF THE PRIOR ART

Water absorbent resins have been extensively used for hygienic materials such as paper diapers, sanitary materials, etc. as a material which can replace pulp or water absorbent paper, based upon its marvelous water absorbency, as well as for applications as water retaining material, water sealing material, etc. and food processing applications making use of their characteristics.

For water absorbent resins applied for hygienic materials, neutralized salts of polyacrylic acid or polymethacryl acid are generally used from the viewpoint of composition. However, when they are used for paper diapers, they should exhibit not only simply high water absorbency under a pressure-free state (absorption rate of urine at no load), but also high water absorbency under loading (absorption rate with load). In order to increase the water absorbency under loading, the crosslinking degree must be increased because the water absorbent resin must absorb urine and other liquids while overcoming the load. However, in the conventional method, if the dosage of copolymerizable crosslinking agent is increased for uniform crosslinking, the water absorbency under loading is increased by the increase of crosslinking degree but has a defect of decreasing the water absorbency under a pressure-free state. This decreasing of the water absorbency under pressure-free state restrains the improvement of the water absorbency under loading.

To solve this problem, methods have been proposed for lowering the crosslinking degree of the inner part of the water absorbent resin in order to maintain the water absorbency under a pressure-free state, and crosslinking the vicinity of the surface of a water absorbent resin particle with a crosslinking agent having at least 2 functional groups which react with the carboxylic acid group and/or carboxylic acid salt group. That is, surface crosslinking methods have been proposed. In this event, for the crosslinking agent, epoxy compounds represented by ethylene glycol diglycidyl ether, etc. (e.g. Japanese Patent Application Laid Open No. 57-44627), polyhydric alcohol represented by glycerin (e.g. Japanese Patent Application Laid Open No. 58-180223), polyvalent amine compounds, polyaziridine compounds, or polyvalent isocyanate compounds (e.g. Japanese Patent Application Laid Open No. 59-189103), polyvalent epoxy compounds having an amino group (e.g. Japanese Patent Application Laid Open No. 63-195205), and reactants of epihalohydrin with a low-molecular primary amine such as ammonia or ethylene diamine (e.g. Japanese Patent Application Laid Open No. 2-248404) are known.

However, because these crosslinking agents have a comparatively low molecular weight, the crosslinking agent penetrates comparatively deeply into the inside of the particles when surface crosslinking takes place. As a result, the inside of the particles is crosslinked, though it is not as much as that observed in uniform-crosslinking, and the water absorbency under pressure-free state decreases.

When polyhydric alcohol or polyvalent amine is used for the crosslinking agent, heating exceeding 180° C. is generally required to have the crosslinking reaction take place, and treatment at such a high temperature brings about thermal crosslinking or thermal deterioration of the water absorbent resin itself. This results not only in difficulty of control over the crosslinking degree but also decreasing of the water absorbency under a pressure-free state as well as water absorbency under loading.

In addition, the crosslinking agents such as epoxy compounds represented by ethylene glycol diglycidyl ether, etc., epoxy compounds containing amino groups in the molecule, polyvalent amine compounds, polyaziridine compounds, or polyvalent isocyanate compounds are comparatively irritating to skin, producing worries about safety when unreacted crosslinking agent remains if they are used as a crosslinking agent of the water absorbent resin for hygienic materials which are likely to come in contact with the skin of babies and infants.

On the other hand, when reactants of epihalohydrin with ammonia or low-molecular primary amine such as ethylenediamine are used for the crosslinking agent, the reactant is a compound in which the amine is simply added to the epoxy group of epihalohydrin, and because no active functional group exists in the molecule of this compound, no effective crosslinking takes place even if heated and the improvement of water absorbency under loading is insufficient.

SUMMARY OF THE INVENTION

An object of the present invention is to provide a process for the production of water absorbent resin using crosslinking agents for surface crosslinking which can efficiently crosslink the vicinity of the surface of the water absorbent resin and are highly safety, and which provide a water absorbent resin having high water absorbency both under loading and pressure-free state.

The present invention relates to a process for the production of water absorbent resin comprising a step of adding 0.01–10 parts by weight of a high molecular crosslinking agent (B) having at least two azetidinium salt groups in the molecule and having a weight average molecular weight of at least 1000 to 100 parts by weight of water absorbent resin particles (A) having carboxylic group and carboxylic acid salt group, and by heating and crosslinking the vicinity of the surface of the water absorbent resin particles (A).

DETAILED DESCRIPTION OF THE INVENTION

According to the present invention, as the water absorbent resin particles (A), there is no particular limitation as long as they are water absorbent resin particles having carboxylic acid and/or carboxylic acid salt groups, and examples include the crosslinked partially neutralized polyacrylic acids, self-crosslinked partially neutralized polyacrylic acid, crosslinked copolymers of starch-grafted acrylic acid salt, hydrolyzates of crosslinked copolymers of starch-grafted acrylonitrile, copolymers of vinyl alcohol-acrylic acid salt, crosslinked copolymers of acrylic acid salt-acrylamide or partial hydrolyzates of crosslinked copolymer of acrylic acid salt-acrylonitrile, crosslinked copolymers of acrylic acid salt and 2-acrylamide-2-methylpropane sulfonic acid salt, neutralized copolymers of crosslinked isobutylene-maleic acid anhydride, and crosslinked carboxymethylcellulose salt, and one or more types of these resins may be used.

The preferable ones among them may include water absorbent resin having a large number of carboxylic groups and/or carboxylic acid salt groups, that is, crosslinked partially neutralized polyacrylic acid and self-crosslinked partially neutralized polyacrylic acid, in view of the water absorbing properties of the water absorbent resin finally obtained.

In the meantime, examples for the salts used as a carboxylic acid salt include the sodium salt, potassium salt, ammonium salt, lithium salt or the like. The most preferable one among them is the sodium salt.

The manufacturing method and shape of the water absorbent resin particles (A) are not particularly limited, and examples include a pearl-like form obtained by the reverse phase suspension polymerization, and the lamellar, lumpy, rocky, granular, or amorphous form obtained by grinding dried water absorbent resin obtained after aqueous solution polymerization. Granulated water absorbent resins which are produced by granulating water absorbent resin particles are also usable.

The size of the water absorbent resin particles (A) is not particularly defined, and is usually around 10–140 mesh. However, when these resins are applied for hygienic materials such as paper diapers, fine particles with large surface area are absorbed so rapidly that lateral diffusion of urine is prevented and further finer particles tend to drop out of the pulp layer of the base material. Therefore, it is generally preferable that 20–60 mesh particle sizes account for 70 wt % or more of the total volume, and more preferably, 20–42 mesh particle sizes account for 70 wt % or more of the total volume.

In the present invention, the high molecular crosslinking agent (B) having two or more azetidinium salt groups is a compound which is synthesized by condensation reaction of high molecular polyamine compounds generally having at least two secondary amino groups in a molecule (1) with epihalohydrin (2).

The fact that polymers containing azetidinium salt groups are obtained by a condensation reaction between the high molecular polyamine compound (1) and epihalohydrin (2) is described, for example, in Page 233–236, Appita, Vol. 37 (No. 3), 1983. The azetidinium salt referred to herein has the structure of the reaction product shown in the model reaction formula below.

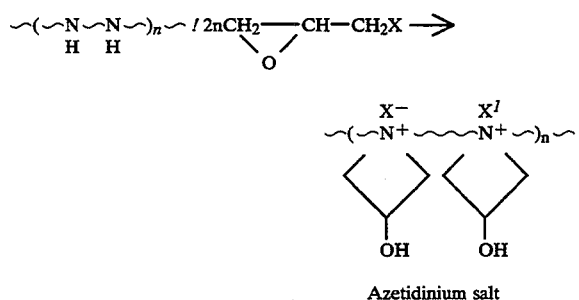

Azetidinium salt (where, in the above formula, X denotes Cl, Br, or I, and n denotes an integer of 1 to 1000.)

As amine compounds, if primary polyamine compounds are used for condensation with epihalohydrin, addition reactions between primary amine and epoxy group and quaternization reaction between molecules predominate. Thus the ring closure reaction in the molecule which generates the azetidinium salt group, which is the highly active group with carboxylic acid and carboxylic acid salt groups, does not take place successfully. When tertiary amine compounds are used, the ring-closing reaction itself does not occur, and it is not preferable.

Examples of high molecular polyamine compound (1) having at least two secondary amino groups include polyethylenimine compounds, which are polymers of ethylenimine; condensation type high molecular polyamine compounds obtained by the condensation reaction of a polyglycidyl ether compound (pentaerythritol polyglycidyl ether, polyglycerol polyglyglycidyl ether, etc.) with a low molecular amine compound (ethylene diamine, diethylene triamine, triethylene tetramine, tetraethylene pentamine, pentaethylene hexamine, diethanol amine, triethanol amine, etc.); a high-molecular polyamine compound in which an amine compound (monoamine compound, diamine compound, polyamine compound, etc.) is added to the above-mentioned polyvalent glycydyl ether compound; high-molecular polyamine compounds, in which the above mentioned amine compounds are added to polymers of glycidyl (meth)acrylate (polyglycidyl (meth)acrylate, polyaryl glycidyl ether, etc.) (where, "... (meth)acryl ... " means "... acryl ... " or "... methacryl ... " and the same applies hereinafter); addition type high-molecular polyamine compounds obtained by reacting an olefin type compound, which is capable of Michael addition reaction with amines, (ethylene glycol diacrylate, glycerol diacrylate, glycerol triacrylate, trimethylol propane diacrylate, trimethylol propane triacrylate, pentaerythritol polyacrylate, etc.), with the above-mentioned low-molecular polyamine compounds; addition type high-molecular polyamine compounds which are addition products of the compounds having an olefin group capable for Michael addition to the epoxy group in the molecule (glycydyl (meth)acrylate, etc.) and the above-mentioned low-molecular polyamine; and mixtures of two or more types of these. Of these, preferable ones are high-molecular polyamine compounds which have at least four secondary amino groups in the molecule.

If the compound having the amide group in the molecule as the high-molecular polyamine compound (1) (e.g. polyamide polyamine compounds including condensation reaction products of adipic acid with diethylene triamine) is used, imidization reaction between amide groups occurs, with generation of ammonia gas. As a result, breaking of main chain of the polyamine compounds occurs. Thus, this is not preferable. In addition, allowing the amide group to enter the molecular chain not only increases the secondary amine equivalent but also results in nonuniform distribution of secondary amine groups in the molecule, which is also not preferable.

Examples of epihalohydrin (2) include epichlorohydrin, epibromohydrin, epiiodohydrin, and the like.

The condensation reaction of the high molecular polyamine compound (1) and epihalohydrin (2) can be achieved by adding epihalohydrin (2) to high-molecular polyamine compound (1) and heat-reacting them, usually for several hours at 20°–100° C. With this condensation reaction, the high-molecular crosslinking agent (B) having two azetidinium salt groups of the present invention is synthesized.

The amount of epihalohydrin (2) with respect to the high-molecular polyamine compound (1) is generally 10–200 mol % with respect to the content of secondary amino group in the polyamine compound, preferably 50–150 mol %.

If the dosage of epihalohydrin is less than 10 mol %, the content of azetidinium salt group in the high-molecular crosslinking agent (B) becomes so low that the activity becomes too low, causing not only the unsuccessful crosslinking reaction with water absorbent resin particles (A) but also a large volume of amino group to be left in the molecule. This is not preferable also in view of the safety of the crosslinking agent itself.

On the other hand, if the dosage of epihalohydrin exceeds 200 mol %, a large volume of unreacted epihalohydrin remains in the condensation product; this is not only uneconomical but also unpreferable from the viewpoint of safety.

The weight-average molecular weight of the high-molecular crosslinking agent (B) in the present invention is, in general, 1,000 or more, preferably, 5,000–100,000, and more preferably, 10,000–100,000.

If the weight-average molecular weight is less than 1000, when the high-molecular crosslinking agent (B) is added to the water absorbent resin particles (A), it permeates relatively far inside the water absorbent resin particles (A) and crosslinking takes place even inside the particle, lowering the water absorbency under a pressure-free state. In addition, if the low-molecular compound with comparatively high permeability to the skin remains unreacted in the water absorbent resin, there may be concerns with safety.

On the other hand, if the weight-average molecular weight exceeds 100,000, when the high-molecular crosslinking agent (B) is added to the water absorbent resin particles (A) as it is or in the form of aqueous solution, excessively high viscosity of the high-molecular crosslinking agent (B) or the aqueous solution of the high-molecular crosslinking agent (B) prevents uniform addition, and as a result, not only is water absorbent resin with sufficient water absorbency under loading difficult to obtain, but also the flowability of the water absorbent resin obtained may decrease.

The number of functional groups of azetidinium salt of the high-molecular crosslinking agent (B) is at least 2, preferably 4 or more. If the number of functional groups of azetidinium salt is less than 2, the crosslinking reaction does not proceed. Consequently, improvement of water absorbency under loading is not recognized.

After the condensation reaction of the high-molecular polyamine compound (1) with epihalohydrin (2), it is possible to add acid as required to adjust to pH 4–9, preferably pH 5–8.

As the acid to be added, any acid which does not react with the azetidinium salt group is acceptable, and examples include phosphoric acid, hydrochloric acid, sulfuric acid, and nitric acid.

In the present invention, the ratio of the high-molecular crosslinking agent (B) to the water absorbent resin particles (A) varies in accordance with the type of the high-molecular crosslinking agent (B), the type of the water absorbent resin particles (A), and the crosslinking degree, as well as the desired performance of the water absorbent resin obtained, but it is generally 0.01–10 parts in weight ratio to 100 parts of the water absorbent resin particles (A), preferably 0.05–5 parts, more preferably 0.1–3 parts. If the dosage of this high-molecular crosslinking agent (B) is less than 0.01 parts, the crosslinking effects are not brought out successfully and improvement of water absorbency under loading is poor, while if the dosage exceeds 10 parts, the crosslinking density becomes so large that both water absorbency under pressure-free state and that under loading lower.

There is no particular limitation to the method to add the high-molecular crosslinking agent (B) to the water absorbent resin particles (A), but examples include a method to agitate and mix after the high-molecular crosslinking agent (B) is added to the water absorbent resin particles (A), a method in which while the water absorbent resin particles (A) are stirred, the high-molecular crosslinking agent (B) is added to (A), a method in which while the water absorbent resin particles (A) are stirred at high speed, the aqueous solution of the high-molecular crosslinking agent (B) is added by spraying, and the like.

In the present invention, further adding an aqueous solution of a water soluble compound (C) together with the high-molecular crosslinking agent (B) enables uniform addition of the high-molecular crosslinking agent (B) to the surface of the water absorbent resin particles (A). In this event, the method to use both the high-molecular crosslinking agent (B) and water soluble compound (C) is not particularly limited, and examples include a method to add the high-molecular crosslinking agent (B) and water soluble compound (C) separately to the water absorbent resin particles (A), a method to add an aqueous solution which includes both the high-molecular crosslinking agent (B) and water soluble compound (C) to the water absorbent resin particles (A), and the like.

The water soluble compound (C) is at least one selected from the group consisting of an alkylene oxide adduct of monofunctional alcohol (a) and lactams (b) and which is inert to the above-mentioned water absorbent resin particles (A) and high-molecular crosslinking agent (B).

Examples of an alkylene oxide adduct of monofunctional alcohol (a) include ethylene oxide adduct of methanol, ethylene oxide adduct of ethanol, ethylene oxide adduct of butylalcohol, ethylene oxide/propylene oxide (block or random) adduct of methanol, and the like. The number of carbon atoms of the above-mentioned monofunctional alcohol component is preferably about 1–5, and the number of carbon atoms of the alkylene group of the alkylene oxide component is preferably about 2–4.

Examples of lactams (b) include $\beta$-propiolactam, $\gamma$-butyrolactam, $\delta$-valerolactam, and $\epsilon$-caprolactoam. The number of carbon atoms of the lactams (b) is preferably 3–9.

Of the examples of these water soluble compounds (C) mentioned above, more preferable ones are ethylene oxide adducts of monofunctional alcohol, and particularly preferable ones are ethylene oxide 2 to 10 mols adduct of monofunctional alcohol.

According to the present invention, the concentration of the aqueous solution of the water soluble compound (C) may vary in accordance with the type of the water soluble compound (C), but it is preferable to set the concentration of the water soluble compound (C) so that the absorbency of the water absorbing resin particles (A) to the aqueous solution of the water soluble compound (C) is 5 times or less, preferably 3 times or less. This concentration is generally 2–70 wt %, preferably 5–60 wt %. For example, if the alkylene oxide adducts of monofunctional alcohols (a) are used as the water soluble compound (C), 10–60 wt % concentration is particularly preferable, and if lactams (b) are used for the water soluble compound (C), 5–40 wt % concentration is particularly preferable.

If the aqueous solution concentration of the water soluble compound (C) is less than 2 wt %, the water absorbency of the water absorbent resin particles (A) to the aqueous solution exceeds 5 times. In this case, when the water absorbent resin particles (A) are treated with the mixture aqueous solution, the water absorbent resin particles (A) become half-swollen and coagulation occurs between swollen particles to easily form lumps; this makes it difficult to uniformly crosslink the surface vicinity of the water absorbent resin particles (A). As a result, the water absorbency under loading of the obtained water absorbent resin is decreased. On the other hand, when the aqueous solution concentration of the water soluble compound (C) exceeds 70 wt %, a large volume of aqueous solution is required for treatment in order to secure the water volume necessary for crosslinking reaction between the water absorbent resin particles (A) and high-molecular crosslinking agent (B), which is uneconomical.

The addition amount of the aqueous solution of the above water soluble compound (C) can be varied in accordance with the type and the concentration of the aqueous solution of the water soluble compound (C) but it is generally 0.1–10 parts by weight with respect to 100 parts of the water absorbent resin particles (A), preferably 1–8 parts by weight, and particularly preferably 2–5 parts by weight. Addition of less than 1 weight part of the aqueous solution of the water soluble compound (C) results in poor effects on adding the high-molecular crosslinking agent (B) to the vicinity of the surface of the water absorbent resin particles (A), whereas the addition amount exceeding 10 parts by weight not only requires a longer time for crosslinking reaction but also may lower the absorbency of the obtained water absorbent resin, which is impractical.

For the apparatus used for adding the high-molecular crosslinking agent (B) or aqueous solution of high-molecular crosslinking agent (B) and water soluble compound (C), any ordinary blender is acceptable. Examples include a cylindrical blender, a screw blender, a screw extruder, a turbulizer, a Nauta blender, a V-shaped rotating mixer, a ribbon blender, a double arm type kneader, a fluidized bed mixer, an air blender, a rotating disc type mixer, and a roll mixer.

The temperature at which the surface vicinity of the water absorbent resin particles (A) obtained by processing as mentioned above is crosslinked by heating, varies in accordance with the type and amount of the high-molecular crosslinking agent (B) or the volume of water in the aqueous solution (C), but in general, it is 80°–180° C., preferably 100°–160° C. At temperatures less than 80° C., a long time is required for crosslinking reactions, which is not only uneconomical but also causes the crosslinking reaction not to take place successfully for allowing the effects of the present invention, and as a result, water absorbent resin with excellent water absorbency under loading cannot be obtained. On the other hand, at temperatures exceeding 180° C., coloring of the water absorbent resin or decreasing of water absorbency by heat crosslinking occurs. This heat-crosslinking would take place simultaneously with the above mixing.

For the equipment used for this heat crosslinking, ordinary driers or heaters are acceptable. Examples include a hot-air drier, a rotary drier, a paddle drier, a rotating disc drier, a fluidized bed drier, a belt type drier, a Nauta type heater, and an infrared drier.

This heating may be carried out in vacuum or in an inert gas flow atmosphere as required. Heating in vacuum or in the inert gas flow atmosphere suppresses coloring, oxidation, or thermal deterioration of the water absorbent resin even if heat-crosslinking is carried out at higher temperature. For the examples of the inert gas flow, nitrogen, helium, or carbon dioxide may be listed among others.

The depth of the surface-crosslinking from the surface of the water absorbent resin particles in this invention—the vicinity of the surface being crosslinked by a crosslinking agent—is varied, depending on the particle size of the water absorbent resin particles (A) and the target of the performance of obtainable improved water absorbent resin. However, the depth is generally 40% or less, preferably 20 % or less, more preferably 10% or less than the radius of the water absorbent resin particles (A).

The absorbency of the water absorbent resin obtained by the present invention can be varied in accord with the application purposes of the water absorbent resin, but the water absorbency under a pressure-free state (water absorbency at no load) to an isotonic sodium chloride solution is, in general, 50 g/g or higher, and preferably 55 g/g to 100 g/g. In addition, the water absorbency under loading (water absorbency at load) to the isotonic sodium chloride solution is, in general, 30 g/g or higher, and preferably 35 g/g to 60 g/g. The isotonic sodium chloride solution referred here is a 0.9 wt % aqueous solution of sodium chloride.

The water absorbent resin with excellent water absorbency under loading such as that of the present invention can be suitably applied as the absorbent for hygienic materials such as paper diapers, sanitary materials, and the like. In particular, when it is applied to paper diapers, not only the absorbency of paper diapers is improved but also it improves the dry touch of the paper diaper surface or reduction of leakage after urine is absorbed.

The water absorbent resin of the present invention can be admixed with the antiseptic agent, fungistat, disinfectant, antioxidant, ultraviolet-absorbers, coloring agent, perfumes, deodorants, inorganic powders, and organic fibrous materials at any optional stage in the method according to the present invention.

Hereinafter, the invention is further described below by referring to Examples and Comparative Examples, but it must be noted that the invention is not limited to those. Hereinafter, parts represent the parts by weight and % represents wt %.

The performance of the water absorbent resin according to the present invention was measured by the following methods.

Water absorbency under pressure-free state:

One gram of the water absorbent resin was placed in a tea bag prepared with 250-mesh nylon net and immersed in an isotonic sodium chloride solution (concentration: 0.9 wt %) for 30 minutes; then, it was pulled up, drained for 15 minutes, and measured for an increase of weight. The value is designated as water absorbency under a pressure-free state.

Water absorbency under loading:

In a cylindrical plastic tube (30 mm in inside diameter, 60 mm high) with a 250-mesh nylon net affixed on the bottom surface, 0.1 g of the water absorbent resin was placed and uniformly spread, on which a weight 30 mm in outside diameter was placed so that a 20 g/cm$^2$ load was applied. A tube containing the water absorbent resin was immersed in a Petri dish (vessel 12 cm in diameter) containing 60 ml of the isotonic sodium chloride solution, and left standing with the nylon net side down for 30 minutes. The 10-fold value of the increase in weight after 30 minutes was designated as water absorbency under loading.

Flowability of water absorbent resin (index):

Using the powder tester (manufactured by Hosokawa Micron Corporation), four items, namely the angle of repose, angle of spatula, compressibility, and particle distribution of the water absorbent resin powders, were measured and the flowability index was given. The relationship between the flowability index and the easiness of powder flowing is given as follows:

Flowability indices:
80 or higher: extremely good flowability
70–80: good flowability
60–70: slightly poor flowability
60 or less: poor flowability Evaluation of dry feeling by paper diapers (1) Preparation of model paper diapers: On a polyethylene sheet cut in the size of 14 cm × 36 cm, tissue of the same size and 200 g/m$^2$ basic weight fluff pulp were overlapped. Then, 5 g of water absorbent resin was uniformly sprinkled over the fluff pulp, and 200 g/m$^2$ basic weight fluff pulp, tissue, and non-woven fabric were overlapped in this order. By pressing this laminate at 5 kg/cm$^2$ pressure for 90 seconds, a model paper diaper is produced.

(2) Measurement of dry feeling: 150 ml of artificial urine (aqueous solution containing 0.9% sodium chloride, 8% urea, 0.03% magnesium sulfate, 0.03% calcium chloride) was poured at the center of the model paper diaper, and the dry feeling at the paper diaper surface after 30 minutes was evaluated with finger touching by 10 panelists, and the mean value was indicated with the following four stages:

◎ : good dry feeling
○: satisfactory dry feeling but slightly poorer than ◎
△: poor dry feeling with slight slippery feeling
×: very slippery Production Example 1 [synthesis of high-molecular crosslinking agent ①]

In a 500-ml reaction container equipped with a stirrer, 43 parts of polyethyleneimine of about 10,000 molecular weight ("Epomine SP-200" manufactured by NIPPON SHOKUBAI CO., LTD.) and 153 parts of water were placed and heated to 60° C. While the temperature of the content was kept at 60° C., 92.5 parts of epichlorohydrin was gradually added dropwise using a dropping funnel over 1 hour, and stirring was continued for 5 hours at 60° C. to react them. After completion of reaction, 11.5 parts of hydrochloric acid (36% solution) were added and the mixture was stirred for a further 2 hours at 60° C., and an aqueous solution of a high-molecular crosslinking agent ① (crosslinking agent concentration: 50%) was obtained.

The pH of this high-molecular crosslinking agent ① aqueous solution was 5.3 and the weight-average molecular weight measured with the gel permeation chromatography (GPC) was about 22,000.

Production Example 2 (synthesis of high-molecular crosslinking agent ②)

In a 1000-ml reactant container equipped with a stirrer, 87 parts of ethylene glycol diglycidyl ether and 300 parts of triethylene glycol monomethyl ether were placed and heated to 50° C. With the temperature of the content kept at 50° C., 30 parts of ethylene diamine were gradually added dropwise using a dropping funnel over 2 hours, and by allowing them to react by continuing agitation at 50° C. for 6 hours, ethylene glycol diglycidyl ether and ethylene diamine were condensed and the reactant containing a large volume of secondary amino groups in the molecule was obtained. Then, the temperature of the content was heated to 60° C. and 140 parts of epibromohydrin were gradually added dropwise over 2 hours, and the mixture was stirred at 60° C. for a further 5 hours to continue reaction. Upon completion of the reaction, 15 parts of phosphoric acid and 300 parts of water were added, and the mixture was stirred at 60° C. for a further 2 hours, and the aqueous solution of high-molecular crosslinking agent ② (crosslinking agent concentration: 30%) was obtained.

The pH of this high-molecular crosslinking agent ② aqueous solution was 6.1 and the weight-average molecular weight measured with GPC was about 31,000.

Production Example 3 (synthesis of high-molecular crosslinking agent ③)

In a 1000-ml reactant container equipped with a stirrer, 85 parts of ethylene glycol diacrylate and 200 parts of ethylene glycol monomethyl ether were placed and heated to 30° C. With the temperature of the content kept at 30° C., 51 parts of diethylene triamine were gradually added dropwise using a dropping funnel over 2 hours, and by allowing them to react by continuing stirring at 30° C. for 6 hours, ethylene glycol diacrylate and diethylene triamine were condensed by the Michael addition reaction and the reactant containing a large volume of secondary amine in the molecule was obtained. Then, the temperature of the content was heated to 60° C. and 92.5 parts of epibromohydrin were gradually added dropwise over 2 hours. and the mixture was stirred at 60° C. for a further 5 hours to continue the reaction. Upon completion of reaction, 10 parts of phosphoric acid and 200 parts of water were added, and the mixture was stirred at 60° C. for a further 1 hour, and the aqueous solution of high-molecular crosslinking agent ③ (crosslinking agent concentration: 37%) was obtained. The pH of this high-molecular crosslinking agent ③ aqueous solution was 5.8 and the weight-average molecular weight measured with GPC was about 15,000.

Production Example 4 [synthesis of high-molecular crosslinking agent ④]

The process of Example 1 was repeated, except using polyethyleneimine having about 100,000 of molecular weight ("Epomine P-1020" manufactured by NIPPON SHOKUBAI CO., LTD.) in place of polyethyleneimine having about 10,000 of molecular weight, and a high-molecular crosslinking aqueous solution ④ (crosslinking agent concentration: 50%) was obtained.

The pH of this high-molecular crosslinking agent ④ aqueous solution was 5.3 and the weight-average molecular weight measured with the Eel permeation chromatography (GPC) was about 260,000.

EXAMPLE 1

To 1000 parts of the 25% aqueous solution of acrylate-based monomer comprising 72 mol % of sodium acrylate, 27.95 mol % of acrylic acid, and 0.05 mol % of methylene bisacrylamide, 0.01 parts of hydrogen peroxide and 0.02 parts of ascorbic acid were added and adiabatically polymerized at the initial polymerization temperature of 10° C. for 5 hours in the nitrogen atmosphere, and a gel polymer was obtained. After this gel polymer was dried in a belt type hot air dryer set at 150° C., it was ground into particle sizes of 20–60 mesh and water absorbent resin particles (a) were obtained. The particle size distribution in the water absorbent resin (a) was measured and ratio of 20–42 mesh particles are 75% of the total water absorbent resin.

One hundred parts of the water absorbent resin particles (a) were placed in a 2000-ml juicer mixer, and with stirring at a high speed, 1 part of the aqueous solution of high-molecular crosslinking agent ① obtained in the Production Example 1 was diluted with 4 parts of water, then the solution was sprayed and thoroughly mixed. The mixture obtained was heat-treated at 150° C. for about 30 minutes and the water absorbent resin [1] of the present invention was obtained.

The water absorbency under pressure-free state, water absorbency under loading, and powder fluidity of the water absorbent resin particles (a) and the water absorbent resin [1] of the present invention, as well as dryness with model paper diaper were measured and the results are shown in Table 1.

EXAMPLE 2

100 parts of the water absorbent resin particles (a) obtained in the Example 1 were placed in a 2000-ml juicer mixer, and with stirring at a high speed, 5 parts of the mixed aqueous solution of 1 part of the aqueous solution of the high-molecular crosslinking agent ①, 2 parts of water and 2 parts of triethylene glycol monomethyl ether were sprayed and thoroughly mixed. The obtained mixture was heat-treated at 150° C. for about 30 minutes and the water absorbent resin [2] of the present invention was obtained.

The performance measurement results of the obtained water absorbent resin [2] are shown in Table 1.

EXAMPLE 3

The water absorbent resin [3] was obtained in the same manner as in the Example 1, except that 5 parts of aqueous solution mixture comprising 1.5 parts of the aqueous solution of the high-molecular crosslinking agent ② obtained in the Production Example 2, 2 parts of water and 1.5 parts of triethyleneglycol monomethyl ether were used in place of the aqueous solution in which 1 part of the aqueous solution of high-molecular crosslinking agent ① was diluted with 4 parts of water in Example 1.

The performance measurement results of the obtained water absorbent resin [3] are shown in Table 1.

EXAMPLE 4

The water absorbent resin [4] was obtained in the same manner as in Example 1, except that 5 parts of an aqueous solution mixture comprising 1.5 parts of the aqueous solution of the high-molecular crosslinking agent ③ obtained in the Production Example 3, 2 parts of water and 1.5 parts of triethyleneglycol monomethyl ether were used in place of the aqueous solution in which 1 part of the aqueous solution of high-molecular crosslinking agent ① was diluted with 4 parts of water in Example 1.

The performance measurement results of the obtained water absorbent resin [4] are shown in Table 1.

EXAMPLE 5

The water absorbent resin [5] was obtained in the same manner as in the Example 1, except that the high-molecular crosslinking agent ④ obtained in the Production Example 4 was used in place of the high-molecular crosslinking agent ① in Example 1.

The performance measurement results of the obtained water absorbent resin [5] are shown in Table 1.

EXAMPLE 6

The water absorbent resin [6] was obtained in the same manner as in Example 2, except that the high-molecular crosslinking agent ④ was used in place of the high-molecular crosslinking agent ① in Example 2.

The performance measurement results of the obtained water absorbent resin [6] are shown in Table 1.

EXAMPLE 7

The water absorbent resin [7] was obtained in the same manner as in Example 2, except that 1 part of ε-caprolactam was used in place of 2 parts of triethylene glycol monomethyl ether in Example 2.

The performance measurement results of the obtained water absorbent resin [7] are shown in Table 1.

EXAMPLE 8

The water absorbent resin [8] was obtained in the same manner as in Example 2, except that water absorbent resin particles (b) with 42–200 mesh were used in the method of Example 2.

The performance measurement results of the water absorbent resin particles (b) and the obtained water absorbent resin [8] are shown in Table 1.

EXAMPLE 9

The water absorbent resin [9] was obtained in the same manner as in Example 1, except that 20–40 mesh water absorbent resin particles (c) of crosslinked copolymer of starch-grafted sodium acrylate ("SANWET IM-1000" of Sanyo Chemical Industries, Ltd.) were used in place of the water absorbent resin particles (a) in Example 1.

The performance measurement results of the water absorbent resin particles (c) and the obtained water absorbent resin [9] are shown in Table 1.

Comparative Example 1

The water absorbent resin [10] for comparison was obtained in the same manner as in Example 1, except that 5 parts of 10% aqueous solution of ethylene glycol diglycidyl ether (EGDG) were used in place of the aqueous solution in which 1 part of the aqueous solution of high-molecular crosslinking agent ① was diluted with 4 parts of water in Example 1. The remaining EGDG content in the water absorbent resin [10] was measured with the high-speed liquid chromatography (SHIMADZU CORPORATION, "LC-6A") and about 150 ppm remaining EGDG was detected. The performance measurement results of the obtained water absorbent resin [10] for comparison are also shown in Table 1.

Comparative Example 2

In a 1000-ml reaction vessel equipped with a stirrer, 88 parts of N, N'-dimethylethylenediamine and 270 parts of water were placed and heated to 60° C. With the temperature of the content kept at 60° C., 185 parts of epichlorohydrin were further gradually added dropwise using a dropping funnel over 1 hour and the mixture was continuously stirred at 60° C. for 5 hours to allow the reaction to take place. Upon completion of the reaction, 8 parts of hydrochloric acid (36% aqueous solution) was added and it was continuously stirred at 60° C. for another 2 hours, and the aqueous solution of the crosslinking agent ⑤ was obtained (crosslinking agent concentration: 50 wt %). The pH of the aqueous solution of this crosslinking agent ⑤ was 5.7 and the weight-average molecular weight measured using GPC was about 270. The water absorbent resin [11] for comparison was obtained in the same manner as in the Example 1, except that the same amount of the aqueous solution of the low-molecular crosslinking agent ⑤ synthesized above was used in place of the high-molecular crosslinking agent ① in Example 1.

The performance measurement results of the obtained water absorbent resin [11] for comparison are also shown in Table 1.

Comparative Example 3

3 parts of epichlorohydrin, 0.49 parts of ethylenediamine, and 30 parts of methanol were mixed and stirred, and allowed to react at 50° C. for 15 hours, and the aqueous solution of the low-molecular crosslinking agent ⑥ was obtained.

The pH of this crosslinking agent ⑥ solution was 9.6 and the weight-average molecular weight measured using GPC was about 400.

The water absorbent resin [12] for comparison was obtained in the same manner as in Example 1, except that 5 parts of the aqueous solution in which 1 part of the solution of the low-molecular crosslinking agent ⑥ synthesized above was diluted with 1 part of water were used in place of the aqueous solution in which 1 part of the high-molecular crosslinking agent ① was diluted with 4 parts of water in Example 1. The performance measurement results of the obtained water absorbent resin [12] for comparison are also shown in Table 1.

Comparative Example 4

In a 1000-ml reaction vessel equipped with a stirrer, 146 parts of adipic acid and 260 parts of water were placed and heated to 80° C. With the temperature of the content kept at 80° C., 103 parts of diethylene triamine were gradually added dropwise using a dropping funnel over 4 hours and after completion of dropping, the mixture was continuously stirred at 80° C. for another 3 hours, and the aqueous solution of polyamide polyamine was obtained.

Then, the temperature of the content was cooled to 60° C. and with the temperature of the content kept at 60° C., 92.5 parts of epichlorohydrin were further gradually added dropwise over 1 hour using a dropping funnel, and with continuous stirring at 60° C. for 5 hours, it was allowed to react. Upon completion of the reaction, 6 parts of hydrochloric acid (36% aqueous solution) was added and with continuous stirring at 60° C. for another 2 hours, the aqueous solution of polyamidepolyamine/epichlorohydrin resin ⑦ was obtained (crosslinking agent concentration: 50 wt %).

The pH of the aqueous solution ⑦ was 7.2 and the weight-average molecular weight measured using GPC was about 33,000.

The water absorbent resin [13] for comparison was obtained in the same manner as in Example 1, except that the same amount of the aqueous solution of the polyamide polyamine/epichlorohydrin resin ⑦ synthesized above was used in place of the high-molecular crosslinking agent ① in Example 1.

The performance measurement results of the obtained water absorbent resin [13] for comparison are also shown in Table 1.

Comparative Example 5

The water absorbent resin [14] for comparison was obtained in the same manner as in Example 1, except that 5 parts of 10% aqueous solution of commercially available polyamide polyamine/epichlorohydrin resin ("Kymene 557H" manufactured by Dickhercules Ltd.) were used in place of the aqueous solution in which 1 part of the aqueous solution of high-molecular crosslinking agent ① was diluted with 4 parts of water in Example 1.

The performance measurement results of the obtained water absorbent resin [14] for comparison are also shown in Table 1.

TABLE 1

| | | WAF (g/g) | WAL (g/g) | FI | DR |
|---|---|---|---|---|---|
| Example 1 | Particles (a) | 68 | 6 | 75 | X |
| | Resin [1] | 66 | 37 | 78 | ○ |
| Example 2 | Resin [2] | 67 | 42 | 80 | ◉ |
| Example 3 | Resin [3] | 67 | 43 | 81 | ◉ |
| Example 4 | Resin [4] | 66 | 41 | 82 | ◉ |
| Example 5 | Resin [5] | 65 | 34 | 68 | ○ |
| Example 6 | Resin [6] | 67 | 42 | 73 | ◉ |
| Example 7 | Resin [7] | 66 | 40 | 77 | ◉ |
| Example 8 | Particles (b) | 68 | 4 | 70 | X |
| | Resin [8] | 65 | 40 | 73 | ○ |
| Example 9 | Particles (c) | 65 | 5 | 75 | X |
| | Resin [9] | 64 | 41 | 80 | ◉ |
| Comparative Example 1 | Resin [10] | 54 | 28 | 75 | ○ |
| Comparative Example 2 | Resin [11] | 48 | 26 | 73 | △ |
| Comparative Example 3 | Resin [12] | 65 | 10 | 73 | X |
| Comparative Example 4 | Resin [13] | 58 | 27 | 67 | △ |
| Comparative Example 5 | Resin [14] | 63 | 22 | 64 | △ |

Note:
WAF: Water absorbency under pressure-free state
WAL: Water absorbency under loading
FI: Flowability index
DR: Dryness of paper diaper Thus, the process according to the present invention has the following advantages.

① Because the crosslinking agent used in the manufacturing process of the present invention has high molecular weight, the crosslinking agent does not permeate inside the water absorbent resin particles and crosslinking only the vicinity of the surface of the water absorbent resin particles can be done efficiently.

② Because the high-molecular crosslinking agent used in the present invention has a large number of azetidinium salt groups highly reactive to carboxylic acid salt groups and/or carboxylic acid groups, unreacted crosslinking agent does not remain after heat-crosslinking.

(3) Unlike polyhydric alcohol or polyvalent amine compounds, the high-molecular crosslinking agent used in the present invention is able to surface-crosslink at comparatively low temperatures. Consequently, no thermal crosslinking or coloring of the water absorbent resin occurs at the time of heat-crosslinking.

(4) Because the high-molecular crosslinking agent used in the present invention does not contain any functional group such as amide group which is susceptible to hydrolysis or heat decomposition, excellent hydrolysis resistance and heat stability are secured.

(5) Because the crosslinking agent used in the present invention has high molecular weight, permeability to the skin is low and the absence of the amide group ensures high safety of the crosslinking agent itself.

(6) The use of the aqueous solution of the specific water soluble compound (C) as a solvent for the crosslinking agent can achieve further homogeneous surface crosslinking. That is, because the aqueous solution of this water soluble compound (C) is scarcely absorbed by the water absorbent resin particles, coagulation does not take place between water absorbent resin particles themselves in the process of adding and mixing the crosslinking agent to the water absorbent resin particles and uniform addition and mixture can be carried out with excellent operability ensured.

(7) Because no organic solvent is used, the equipment with explosion-proof construction is not required, achieving good economy and the process to remove the organic solvent is not required, either.

The water absorbent resin obtained in the present invention provides the following features.

(1) High water absorbency both under a pressure-free state and under loading.

(2) High gel strength and excellent shear stability of gel. Good hydrolysis and good thermal stability.

(3) When in contact with water, the water absorbent resin according to the present invention is free from formation of lumps and possesses a proper water absorbing speed.

(4) Good dry feeling of the gel after water absorption.

(5) Good flowability.

(6) Less coagulation of particles due to moisture absorption even under high-humidity conditions.

(7) High compatibility with skin.

In addition, paper diapers using the water absorbent resin obtained by the process of the present invention provide the following features.

(1) Good dry and smooth feelings of the surface of the paper diapers after they absorb urine.

(2) The proper water absorbing speed provided by the water absorbent resin enables good diffusion of urine inside the paper diaper and efficient absorption of urine throughout the paper diaper.

(3) Less leakage of urine from the paper diaper.

With the effects described above, the water absorbent resin according to the present invention can be particularly suited for the water absorbing material for hygienic materials etc. directly in contact with human bodies such as paper diapers for infants or adults, sanitary napkins, incontinence pads, and the like. In addition, it is useful for various applications; e.g. application in contact with foods such as freshness retaining materials, cold retaining materials, drip absorbers, and the like; solidification agents for pet urine; solidification agents for waste blood; desiccants; water retainers for plant, soil, etc.; materials for separating water from oil; sludge solidification agents; anti-dewing agents; water blocking materials or packing materials for civil engineering and construction work purposes; water sealing materials for electric cables and optical fiber cables.

What is claimed is:

1. A process for producing water absorbent resin comprising a step of adding 0.01–10 parts by weight of a high-molecular crosslinking agent (B) which has at least 2 azetidinium salt groups in the molecule and has a weight-average molecular weight of at least 1000 to 100 parts by weight of water absorbent resin particles (A) which have a carboxylic acid group and/or carboxylic acid salt group and a step of heat-crosslinking the vicinity of the surface of the water absorbent resin particles (A).

2. A process for producing water absorbent resin according to claim 1 comprising a step of adding 0.01–10 parts by weight of the high-molecular crosslinking agent (B) and 0.1–10 parts by weight of the 2–70 wt % aqueous solution of a water soluble compound (C) to 100 parts by weight of the water absorbent resin particles (A) and heat-crosslinking the vicinity of the surface of the water absorbent resin particles (A);
wherein the water soluble compound (C) is at least one compound selected from the group consisting of alkylene-oxide adducts of monofunctional alcohols and lactams, and is inert to the water absorbent resin particles (A) and high-molecular crosslinking agent (B).

3. A process for producing water absorbent resin according to claim 1, wherein the weight-average molecular weight of the high-molecular crosslinking agent (B) is 5,000–100,000.

4. A process for producing water absorbent resin according to claim 1, wherein the high-molecular crosslinking agent (B) possesses at least 4 azetidinium salt goups in a molecule.

5. A process for producing water absorbent resin according to claim 1, wherein the high-molecular crosslinking agent (B) does not contain any amide group in a molecule and is a condensation product of high-molecular polyamine having at least 4 secondary amino groups with epihalohydrin.

6. A process for producing water absorbent resin according to claim 1, wherein the ratio of the high molecular crosslinking agent (B) to the water absorbent resin particles (A) is 0.05–5 wt %.

7. A process for producing water absorbent resin according to claim 1, wherein the temperature of heating for crosslinking is 80°–180° C.

8. A process for producing water absorbent resin according to claim 1, wherein the water absorbency under a pressure-free state of the obtained water absorbent resin is 55 g/g to 100 g/g and the water absorbency under loading is 35 g/g to 60 g/g.

9. A process for producing water absorbent resin according to claim 1, wherein the water absorbent resin obtained by the process is useful as a water absorbing agent for hygienic materials.

* * * * *

UNITED STATES PATENT AND TRADEMARK OFFICE
CERTIFICATE OF CORRECTION

PATENT NO. : 5,384,368

DATED : January 24, 1995

INVENTOR(S) : DATE et al.

It is certified that error appears in the above-identified patent and that said Letters Patent is hereby corrected as shown below:

Col. 2, line 4, change "180°C." to —180°C—.

Col. 3, line 52 change "/2n" to —+2n—.

Col. 3, line 55 change "$X^1$" to —$X^-$—.

Col. 11, line 1 change "Eel" to the word —gel—.

Signed and Sealed this

Twenty-second Day of August, 1995

Attest:

BRUCE LEHMAN

*Attesting Officer*     *Commissioner of Patents and Trademarks*